(12) United States Patent
Segal

(10) Patent No.: US 6,754,655 B1
(45) Date of Patent: Jun. 22, 2004

(54) SYSTEMS AND METHODS FOR DIAGNOSING MEDICAL CONDITIONS

(75) Inventor: Michael M. Segal, Chestnut Hill, MA (US)

(73) Assignee: Simulconsult, Inc., Chestnut Hill, MA (US)

( * ) Notice: Subject to any disclaimer, the term of this patent is extended or adjusted under 35 U.S.C. 154(b) by 0 days.

(21) Appl. No.: 09/190,812

(22) Filed: Nov. 12, 1998

Related U.S. Application Data

(63) Continuation-in-part of application No. 09/107,885, filed on Jun. 30, 1998, now Pat. No. 6,212,519.

(51) Int. Cl.[7] .............................................. G06F 17/30
(52) U.S. Cl. ........................ 707/6; 707/104.1; 600/300
(58) Field of Search ................................ 707/1–5, 6–7, 707/9–10, 100–104.1; 705/2–3; 600/300; 706/924; 128/920–925, 898.01, 899, 898

(56) References Cited

U.S. PATENT DOCUMENTS

| | | | | |
|---|---|---|---|---|
| 4,872,122 A | * | 10/1989 | Altschuler et al. | 356/432 |
| 5,594,638 A | * | 1/1997 | Iliff | 705/3 |
| 5,615,112 A | * | 3/1997 | Liu Sheng et al. | 707/104.1 |
| 6,117,073 A | * | 9/2000 | Jones et al. | 600/300 |
| 6,212,519 B1 | * | 4/2001 | Segal | 707/6 |

OTHER PUBLICATIONS

ONCOCIN Medical Expert System, Tu et al., Communications of the ACM, v32, n12, Dec. 1989.*
Horrocks, et al., "Computer–Aided Diagnosis: Description of an Adaptable System, and Operational Experience with 2,034 Cases", British Medical Journal, 1972, vol. 2, pp. 5–9.

* cited by examiner

*Primary Examiner*—Shahid Alam
*Assistant Examiner*—Jean Bolte Fleurantin
(74) *Attorney, Agent, or Firm*—Ropes & Gray, LLP

(57) ABSTRACT

The systems and methods described herein aid a clinician in the diagnostic process by providing the clinician with information about the available clinical procedures that most improve the clinician's ability to reach a correct diagnosis. Specifically, the systems described herein include software tools that can process information about the patient, including age, sex, symptoms, and prior medical history, and information about the known findings associated with different possible medical conditions, and based on this information, rank the other findings that can be ascertained by the clinician to point out to those findings that are most likely to disambiguate between the multiple candidate disease and lead to the correct diagnosis.

31 Claims, 6 Drawing Sheets

SimulConsult: Neurological Syndromes - Microsoft Internet Explorer

File  Edit  View  Go  Favorites  Help

Justification of [ ] [ Hurler syndrome (MPS I-H) ]

Findings PRESENT in this Patient

[✓] Corneal clouding, crystals or opacification
[6m] Kyphosis without scoliosis
[6m] Macrocephaly above the 97th percentile

[ ] In order of
[ ] Differential
[▽] Incidence: Mid
    Rx: None yet
[☑] Onset ages Now  Later
By Now  Later Findings ABSENT in this Patient

[X] Seizures, nonfebrile

[ Profile ]
[ Categories ]
[ Consider ]
[ Modify ]
[ Patient file ]
[ Useful findings ]
[ Differential ]

SYSTEMS AND METHODS FOR DIAGNOSING MEDICAL CONDITIONS

RELATED APPLICATIONS

This application is a continuation-in-part of U.S. Ser. No. 09/107,885, U.S. Pat. No. 6,212,519 entitled "Systems and Methods for Quantifying qualitative medical expressions," filed 30 Jun. 1998, the teachings of which are incorporated by reference.

FIELD OF THE INVENTION

The invention relates to systems and methods for diagnosing medical conditions, and more particularly, to systems and methods that provide information to a clinician during the diagnostic process and that generate and collect information during the diagnostic process to generate records for the patient's medical history.

BACKGROUND OF THE INVENTION

The process of diagnosing an illness or a disease typically involves recording the demographic information about the patient and documenting the findings (symptoms, physical signs and laboratory test results) that the patient is exhibiting. Together the demographic information and the finding information provide a patient profile. The diagnosing physician can compare the demographic information and the finding information of the patient against a listing of the common and descriptive findings for a particular disease, and can determine the likelihood that such a disease would be present in a patient having the information set forth in the profile.

Although, this process is quite simple in principle, in practice the task is actually quite demanding and somewhat of an art, with some doctors being notably better at the diagnostic process than others. There are several factors that complicate the diagnostic process. Firstly, some cases require the consideration of an almost overwhelming number of diseases, reactions and conditions. Secondly, for each disease, the clinician needs to know the symptoms and other findings that are indicative of that particular disease. Additionally, as there can be a considerable overlap of findings between two or more conditions, the clinician must understand which of the findings are particularly useful for making correct diagnosis.

Moreover, even if the clinician does have a strong understanding of the likely diseases and different relevant findings, the clinician must now know how to employ these findings and information in an efficient manner. The efficiency of the diagnostic procedure is of course important. Firstly, the likelihood of a successful treatment occurring often turns on how quickly a medical condition is diagnosed and treated. Moreover, today's cost conscious health management organizations demand that clinicians employ the most cost-effective means for diagnosing a patient's medical condition. Managed care organizations are particularly concerned that clinicians employ the most cost-effective and efficient laboratory testing when diagnosing a patient's medical condition. These concerns are echoed by the medical insurance industry, including federal and state medical reimbursements programs for medical procedures. Accordingly, the diagnosing clinician often faces the problem of having to identify one or two select diagnostic tests to provide findings that can quickly distinguish between several candidate medical conditions to lead to a correct diagnosis of the medical condition afflicting the patient.

Given the complexity of the diagnostic process, and today's emphasis on cost effective health care, a need exists in the medical community to aid clinicians in quickly and efficiently diagnosing a patient's ailment. A further need exists for a system that provides a diagnosing clinician with the sufficient findings to competently and completely consider a plurality of likely medical diseases.

Other objects of the systems and methods described herein will, in part, be set forth below and in part, be obvious to those of ordinary skill in the art from the following description of certain illustrated embodiments.

SUMMARY OF THE INVENTION

The systems and methods described herein aid a clinician in the diagnostic process by providing the clinician with information about the available clinical procedures that most improve the clinician's ability to reach a correct diagnosis. Specifically, the systems described herein include software tools that can process information about the patient, including age, sex, symptoms, and prior medical history, and information about the known findings associated with different possible medical conditions and, based on this information, rank the other findings that can be ascertained by the clinician to identify those findings that are most likely to disambiguate between the multiple candidate disease and lead to the correct diagnosis. To this end the methods and processes described herein include processes for determining which findings are most capable of leading expeditiously to a correct diagnosis. In one practice, the processes evaluate the usefulness of a particular finding by determining a quantitative value representative of how much the presence or absence of a finding affects the probability estimates for a set of known diseases, wherein the probability estimates are representative of the likelihood that a particular disease or condition is the proper diagnosis for the case under consideration.

More specifically, the processes described herein include a process for diagnosing a medical condition of a patient, that includes the acts of providing a plurality of candidate medical conditions, providing a plurality of findings, each of which is representative of clinical information that can be gathered about the patient's condition, determining for each finding, a likelihood that a particular finding can disambiguate between said candidate medical conditions, and ranking the findings as a function of the likelihood that a finding can disambiguate between the plurality of medical conditions, whereby a treating clinician can be provided with useful information regarding the likelihood that a finding can lead to the identification of the target medical condition.

To further aid the clinician, the process can include the further act of weighting the likelihood that a finding can disambiguate between a plurality of medical conditions by a factor representative of an economic cost of obtaining the clinical information representative of the finding. This allows the clinician to determine if effective and inexpensive means are available for reaching the correct diagnosis. Similarly, the process can affect the ranking of findings by weighting the likelihood that a finding can disambiguate between a plurality of medical conditions by a factor representative of a possibility that a disease can be treated effectively. This will direct the clinician to explore diagnosis of more curable diseases and conditions before exploring the possibility that a patient is afflicted by an incurable disease.

To aid the clinician in efficiently collecting useful finding information, the processes described herein can also identify a group of findings that can be determined from a single clinical procedure, and determine a composite score representative of the likelihood that said group of findings can disambiguate between the plural candidate medical conditions. Additionally, the processes can select a plurality of finding that can be identified from a known battery of laboratory tests, and determine a composite score representative of the likelihood that the plurality of findings can disambiguate between the plural medical conditions.

The processes described herein can also provide information to the clinician for allowing the clinician to rule in or rule out certain diagnoses. To that end, the processes can allow a clinician to select one of said plural medical conditions, and determine for the selected medical condition the likelihood that a finding can identify the selected medical condition as the condition afflicting the patient, whereby the clinician can rule in or rule out the selected medical condition. Additionally, the processes can be employed for aiding a clinician in justifying the medical diagnosis reached. For example, the processes can allow for displaying for a patient a listing of findings determined to be present or absence for a patient, and displaying, for a selected medical condition, a set of probabilities each associated with a respective one of findings and each being representative of the likelihood that the respective finding is present in a patient having the selected medical condition, whereby the clinician is provided information for justifying a diagnosis.

To aid the clinician in getting authorization to perform a battery of tests, or any test that can detect the presence or absence of a particular finding, the processes described herein can include the acts of generating a data record representative of the likelihood a particular finding will disambiguate between plural medical conditions, and transmitting the data record to an authorization center for requesting authorization to perform the desired clinical procedure.

BRIEF DESCRIPTION OF THE DRAWINGS

The foregoing and other objects and advantages of the invention will be appreciated more fully from the following further description thereof, with reference to the accompanying drawings wherein;

FIG. 3 depicts a screen shot illustrating a display that provides information as to which of the findings available to the clinician are most useful for disambiguating between a plurality of candidate medical conditions.

FIG. 4 depicts a screen shot illustrating a display that summarizes the justification for each diagnosis being considered;

DETAILED DESCRIPTION OF THE ILLUSTRATED EMBODIMENTS

To provide an overall understanding of the invention, certain illustrative embodiments will now be described, including a system that aids a clinician in identifying those symptoms, conditions or characteristics of a patient that can efficiently lead to a correct diagnosis. However, it will be understood by one of ordinary skill in the art that the systems and methods described herein can be adapted and modified for other suitable applications, including applications outside the medical field, and that such additions and modifications can be made to the invention without departing from the scope hereof.

The invention will now be described with reference to a conventional computer system that is operating under the control of a computer program that configures the computer into a system that implements a process for aiding a clinician in selecting from a plurality of candidate findings, the finding or findings with the greatest likelihood of identifying the correct diagnosis. However, it will be understood that the systems and processes described are provided for illustrative purposes and the invention is not to be limited to the hardware and software described herein, and that other hardware and software can be employed to embody the systems and processes of the invention. For example, dedicated hardware processor systems that are particularly adapted for implementing the processes described herein can be substituted for the conventional computer systems of the exemplary embodiments.

Figure 1:
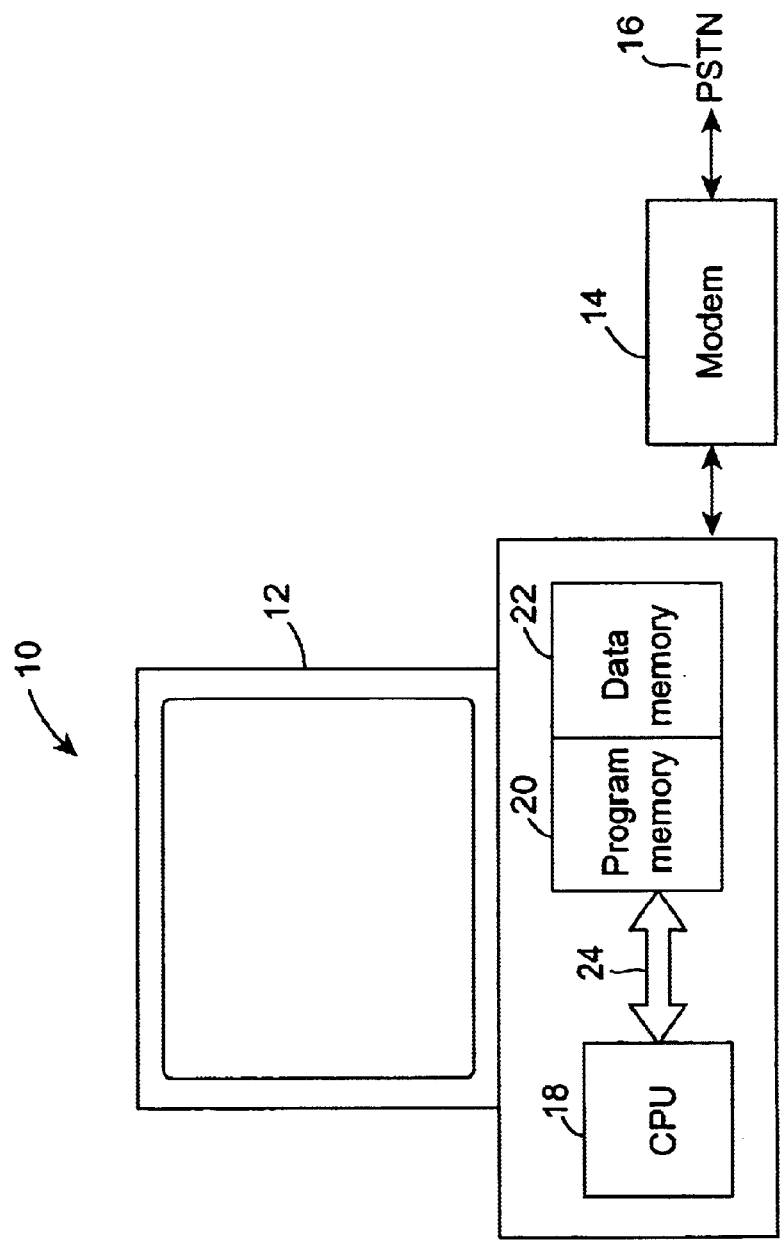
FIG. 1 depicts a computer system for identifying findings relevant to diagnosing a medical condition.

FIG. 1 depicts one diagnostic system that includes a computer program operating on a conventional computer system, such as an IBM PC computer system. Specifically, FIG. 1 depicts a system 10 that includes a conventional computer 12 which connects to a modem 14 which couples the computer 12 to the Public Switching Telephone Network (PSTN) 16. The computer 12 depicted in FIG. 1 includes a CPU 18, a program memory 20, a data memory 22, and a computer bus 24. The CPU 18 can be any conventional central processing unit, and typically will include an arithmetic logic unit, a set of internal registers, and a control unit. The program memory 20 can be a conventional volatile computer memory, such as a circuit card assembly providing random access memory (RAM) for use by the CPU. The data memory 22 can be a persistent memory device such as a hard disk, a floppy disk, or a tape drive. The bus 24 can be a conventional computer bus, such as the ISA bus, which carries data between the CPU 18 and the other elements of the computer system 12.

The computer program can be installed on the persistent memory of the computer 12 and can execute within the program memory 20 of computer 12 under the control of the CPU 18. In this way, the computer program adapts the conventional computer system 12 to operate as a machine for identifying the finding or findings that are most useful in reaching a correct diagnosis.

In one embodiment, the computer program is written as a Java applet that runs within a browser program operating on the computer system 12. As will be understood by one of ordinary skill in the art, a Java applet allows for client side processing. Accordingly, the Java applet described herein can be downloaded from a server located at a remote station. Typically, the Java applet would be downloaded through modem 14 and the PSTN 16 from a Web server located at a remote location. Although the computer program described herein can be written in any high level, or low level language, it will be understood that the Java programming language provides a computer program capable of running on a multiplicity of different platforms, including Windows platforms, Macintosh platforms, UNIX platforms, LINUX platforms, and any other platform that can operate a Java enabled browser. Moreover, the Java programming language is understood to provide compact code, which reduces the download time required for downloading the Java program from the remote Web server.

In one embodiment, the Java program described herein provides a medical diagnostic program that aids a clinician in the diagnosis of a particular disorder, such as a neurological disorder. The program includes an interface that guides the clinician through a series of screens each displayed on the display 12 depicted in FIG. 1. The displays provide the clinician with information as to which findings are most likely to lead to a correct diagnosis of a patient's condition. Findings can include symptoms, patient histories, laboratory test results, environmental factors, the patient's demographic profile or any other information. The program can analyze the identified findings to determine the likelihood that a candidate disease or disorder is the correct diagnosis. The system then employs the likelihood data for the different candidate diseases and processes this likelihood data to determine which of the findings the clinician can still identify which will most likely lead to a conclusive diagnosis. Specifically, the system can process a list of findings that still can be identified by the clinician, and can rank the list of findings according to the likelihood that a listed finding can disambiguate between the possible candidate diseases and lead to a correct diagnosis.

Information about candidate medical conditions and finding information can be stored in the data memory 22 for use by the computer program. In one embodiment, the system includes, or is part of, a computer network, such as the Internet, wherein a plurality of computer systems on the network generate data records representative of diagnostic information about various medical conditions, such as diseases and genetic disorders. The diagnostic information can include a description of the symptoms and other findings that are relevant to the diagnosis of a particular disease, as well as information representative of the probability that a patient with a particular medical condition would have or would lack any of the findings identified in the data record. In the network embodiment, the operation of generating the data records can be distributed across a plurality of users on the network. This allows the distributed building of a database of diagnostic information, and provides a uniform method of generating and capturing data and data records for the database. These data records can be downloaded via the network to computer system data memory 22, to provide a database of finding data that can be directly processed during the diagnostic process. Optionally, a remote database could be processed.

Figure 2:
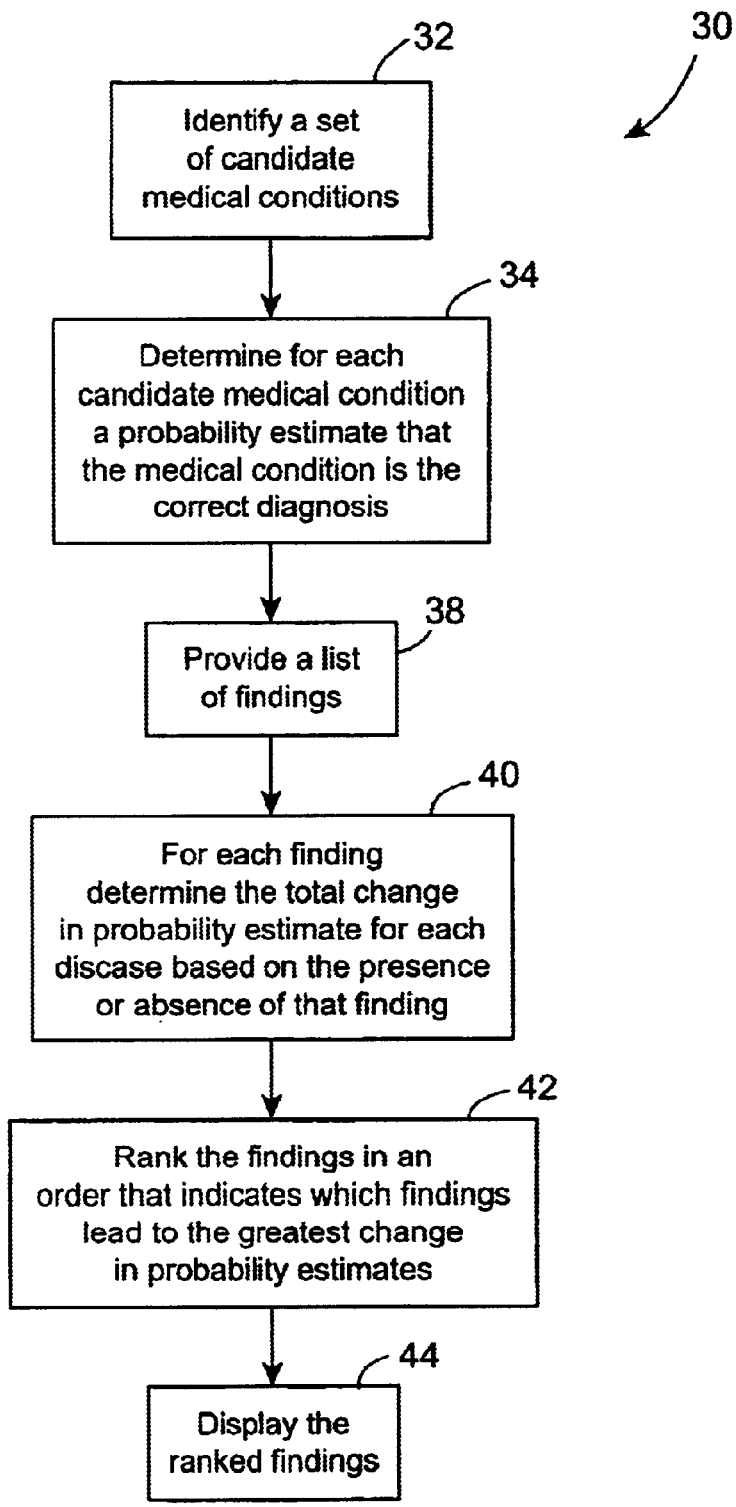
FIG. 2 depicts a process for determining the Usefulness of a finding that can be made during the diagnostic procedure.

FIG. 2 depicts a process 30 for identifying which of the plurality of findings are most useful in selecting between a number of candidates medical conditions to reach a correct diagnosis of a patient's medical condition. The process 30 begins at step 32 in which the process loads a data file that includes information on a set of candidate medical conditions. A candidate medical condition can be a disease, a syndrome, or any kind of statement of health which can be ascertained by the diagnostic procedure. Examples of candidate medical conditions include the normal condition, Trisomy 21 (Down syndrome), fetal alcohol syndrome, epilepsy, diabetes, and any other disease or condition. After step 32, the process 30 proceeds to step 34 where the process determines for each candidate medical condition a probability estimate that the medical condition is the correct diagnosis. The probability estimate can be determined according to any of the known techniques for estimating the likelihood that a candidate suffers from a particular medical condition, including any of the known techniques that determine a probability based on an analysis of empirical data of diagnostic information and patient findings. However, it will be understood by one of ordinary skill in the art that any suitable method can be employed for making these estimations. Probability estimates are constructed using information about the presence or absence of one or more findings.

In an optional embodiment, the probability estimate for a candidate medical condition can depend, in part, on the onset age of the various findings. Accordingly, the probability estimate of a disease can be dependent upon the onset age of a findings, or a set of findings. In non-age dependent models the probability estimate for each disease can be determined using the probability that each finding occurs at all in that disease. In the embodiments depicted in FIGS. 3 through 6, the probability estimates have been determined by employing age dependent models. In age dependent models the probability estimate for each disease can be calculated using the probability that each finding occurs in the disease during the onset period specified for the finding in the patient being considered. Accordingly, a plurality of onset periods can be identified for each finding in each disease, with an associated set of probability estimates being provided for onset of each finding in each disease.

Once the original probability estimates are made for each of the candidate medical conditions, the process 30 proceeds to step 38. In step 38 the process 30 identifies the data file of findings that will be employed during the process. Each finding is representative of information that can be gathered or collected about the patient's medical condition. Findings can include information about the patient's demographics, including the patient's sex, age, race; findings can also include information about symptoms suffered by the patient including vomiting, headaches, seizures, poor reflexes, and other such conditions. Findings can also be the results obtained by laboratory testing including genetic testing, biopsies, or any other suitable types of tests. Once the list of findings is selected, the process 30 proceeds to step 40.

In step 40 the process 30 determines for each finding the total change in probability estimate for each disease based on the presence or absence of that finding. Accordingly, in step 40 the process 30 determines for each finding how much the presence or the absence of that particular finding is likely to affect the probability estimates of the candidate medical conditions identified in step 32. It is understood that the magnitude of the change in the probability estimates for the candidate medical conditions, adjusted for the probability of the finding being present, is a measure of the usefulness of that particular finding for the diagnostic procedure. Once this measure of usefulness has been determined for each finding or for a selected set of the findings, the process 30 can proceed to step 42. In step 42, each of the findings for which a usefulness measure has been determined is ranked in an order that indicates which findings are most likely to lead to the greatest change probability estimates for the candidate medical conditions. Once this ranking has occurred, the process 30 can proceed to step 44, wherein the ranked findings can be displayed to the clinician, such as by displaying the findings as an ordered list presented on a computer display, such as the computer display 12 depicted in FIG. 1. Accordingly, the process 30 provides to the clinician a display of findings which indicates which findings are most likely to lead to the greatest change in probability estimates for the selected candidate medical conditions. It is understood that this measure identifies those findings that are most useful at this step of the diagnostic procedure. It is further understood, therefore, that by performing one of the highly ranked findings, the clinician is performing a step which will most efficiently lead to a correct diagnosis. The ranking of findings (signs, symptoms and lab results) by usefulness provides the clinicians with advice on what to do next, without the need for the clinician to review exhaustively all of the relevant diseases. This feature enables cost-cutting strategies, rapid and standard coded note-taking, and explanations of the likelihood of a disease after doing a set of diagnostic tests.

A Usefulness measure of any particular finding can be determined using two types of inputs. One input is the prior probability that the disease "i" is the correct diagnosis. This probability value, denoted as $p_{Di}$ for Disease "i", denoted as Di, depends on the findings already entered about a particular patient. The second type of input is the probability of a finding "F" having onset in the disease "i" by the current age, or alternatively in a particular age period to be considered, a probability denoted as $P_{F|Di}$, which is obtained entirely from the database stored in data memory 22.

In one implementation, Usefulness of the finding F, denoted as $U_F$, is taken as the sum of the magnitude of Usefulness terms $U_{FDi}$ for each disease "i". Since the finding F can be present or absent in the patient, and there are different changes in the probability of diseases depending on whether F is found to be present or absent, the Usefulness consideration set forth below considers both the possibility of presence of the finding and the absence of the finding. In this implementation, the $U_{FDi}$ terms for F being present or absent are weighted for the probability of F being present ($P_{F\ Present}$) or absent ($P_{F\ Absent}$), as follows:

$$U_{FDi}=|p_{F\ Present}*(\text{disease probability change if } F \text{ is present})|+|p_{F\ Absent}*(\text{disease probability change if } F \text{ is absent})|=|p_{F\ Present}*(\text{new } p_{Di} \text{ for } F \text{ present}-p_{Di})|+|p_{F\ Absent}*(\text{new } p_{Di} \text{ for } F \text{ absent}-p_{Di})|$$

Each of the terms in the $U_{FDi}$ expressions can be computed from the $p_{Di}$ and $p_{F|Di}$ inputs defined previously. Simply by totaling probabilities, $$p_{F\ Present}=\Sigma(p_{Di}*p_{F|Di})$$

where this and all summations are over all diseases "i". Similarly $$p_{F\ Absent}=\Sigma(p_{Di}*(1-p_{F|Di}))=\Sigma p_{Di}-\Sigma(p_{Di}*p_{F|Di})=1-p_{F\ Present}$$

where $\Sigma p_{Di}=1$ since relevant diseases and the normal case are considered. Using Bayes' Theorem, $$\text{new } p_{Di} \text{ for } F \text{ present}=(p_{Di}*p_{F|Di})/i\ p_{F\ Present}$$

and similarly $$\text{new } p_{Di} \text{ for } F \text{ absent}=(p_{Di}*(1-p_{F|Di}))/(1-p_{F\ Present})$$

Substituting in the expression for $U_{FDi}$ $$U_{FDi}=|p_{F\ Present}*(((p_{Di}*p_{F|Di})/p_{F\ present})-p_{Di})|+|(1-p_{F\ Present})*(((p_{Di}*(1-p_{F|Di}))/(1-p_{F\ present}))-p_{Di})|$$

Simplifying terms, $$U_{FDi}=|p_{Di}(p_{F|Di}-p_{F\ Present})|+|-p_{Di}(p_{F|Di}-p_{F\ Present})|$$

Since the absolute values of the two terms are the same, $$U_{FDi}=2*|p_{Di}(p_{F|Di}-p_{F\ Present})|$$

and since $U_{FDi}$ terms are all relative to each other $$U_{FDi}=|p_{Di}(p_{F|Di}-p_{F\ Present})|$$

For this implementation, all the positive changes in probability of diseases are balanced by negative changes in probability since $\Sigma p_{Di}=1$, so in practice only half the $U_{FDi}$ terms need be computed, depending on whether $p_{|Di}-p_{F\ Present}$ is positive. So the overall Usefulness term for a finding in all diseases, $U_F$, can be calculated as follows:

$$U_F=\Sigma U_{FDi}=\Sigma \text{ terms of } (p_{Di}(p_{F|Di}-p_{F\ present})) \text{ in which } p_{F|Di}>p_{F\ Present}$$

In alternative practices, the usefulness measure can also be determined as a function of both the cost of findings (viz. tests) and the curability of diseases, to weight the Usefulness measure to add cost-sensitivity and attention to curability to the Usefulness measure.

Specifically, in cases in which Cost of findings is considered, the Usefulness measures $U_F$ can be corrected for the Cost of the finding (such as cost of a test). In one implementation this is done by dividing each $U_F$ by the cost of the finding. A partial disregard of cost is implemented by dividing each $U_F$ by cost+$50 and a near-complete disregard of cost is implemented by dividing each $U_F$ by cost+$1000. The partial disregard of cost could be also achieved with a different dollar offset figure, or a nonlinear function of cost could be used. Other techniques can be employed without departing from the scope of the invention. It is understood that the addition of cost information allows the clinician to have cost included in the estimates of Usefulness, which provides a way of channeling cost information to clinicians in a way that does not require the clinician to actively pay attention to the cost of tests.

In cases in which the availability of effective treatment, ("Curability") of a disease is considered, the prior disease probabilities $p_{Di}$ are modified to reflect curability for the purposes of the Usefulness determination. In the above described implementation, the effect of Curability is included by multiplying each $p_{Di}$ by 1+C, where C is the Curability number (0 to 100) for a disease in arbitrary units. The $p_{Di}$ terms are then re-normalized such that they once again add up to 1. This addition of Curability information corresponds to the clinical imperative to look harder for more curable diseases. It is noted that the Curability factor has no effect on the probability assigned to the likelihood of a disease; the only effect of the curability adjustment is on the Usefulness determination.

The method for determining Usefulness given above is only one process for determining a factor representative of the ability of a finding to disambiguate between plural candidate medical conditions. Other implementations could be employed including processes modified to include variants on this approach, such as weighting the probability changes by squares of the probability differences instead of absolute values, restricting the analysis to a subset of diseases chosen by their high likelihood, different scaling factors for Cost and Curability features, ignoring or using disease incidence information, and summing Usefulness for all relevant time periods.

Another modification to this Usefulness determination is to group findings so their Usefulness is pooled. As an example, all positive results on chromosome testing, such as abnormal chromosomes demonstrating disease "A" and abnormal chromosomes demonstrating disease "B" are grouped together so the clinician is given a composite score for the Usefulness of checking abnormal chromosomes. Another implementation pools a variety of individual Usefulness values for different findings so they appear as a package, an approach designed to represent a package test performed by a laboratory that is ordered and priced as a group, even though their constituent tests can also be listed separately in the database.

Another modification of the Usefulness determination is helpful during a diagnostic "Rule in/Rule out" procedure. In this practice, Usefulness is computed by calculating the effect of findings only on the disease in question, without calculating the effects on all other diseases as is done for the above-described general case. This simplified calculation conforms to the clinical question of "ruling in" or "ruling out" a specific disease, and can include Curability and Cost modifications, as described above.

Figure 3:
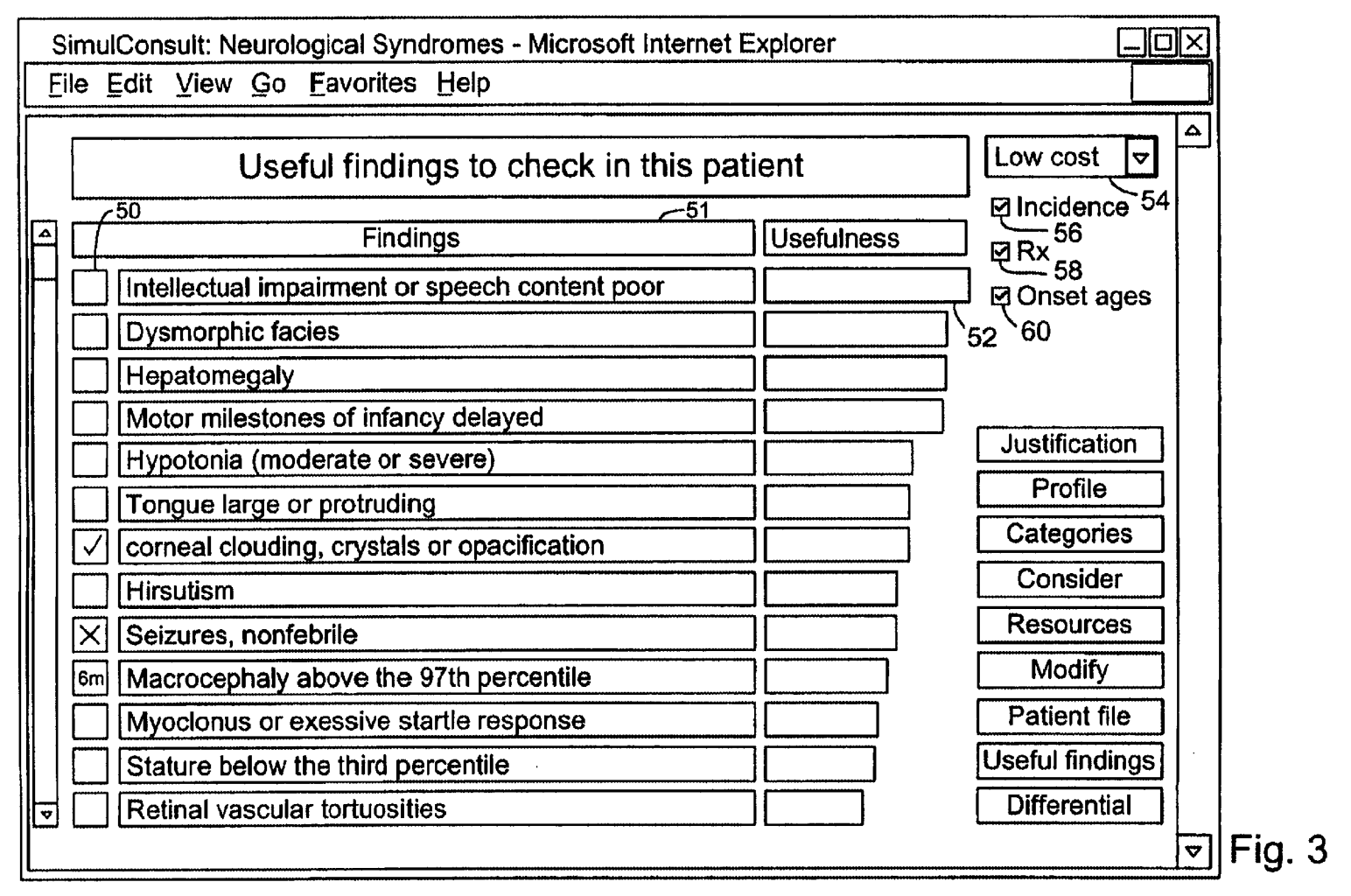

Once measures of usefulness have been computed for each finding, or for each of a number of findings, the findings can be ranked and displayed to the clinician. FIG. 3 depicts a display of a plurality of findings that are ranked from top to bottom according to their usefulness. Continuing with the above-described example, the display illustrated in FIG. 3 can be generated from a Java applet operating on a computer display such as the display 12 depicted in FIG. 1. The illustrated display comprises a set of graphical components arranged on the screen for conveying to a user, such as the clinician, an understanding as to which of the findings are most likely, under the constraints provided, to lead to an efficient diagnosis of the patient's medical condition. As illustrated in FIG. 3, display includes a plurality of findings 51 each presented adjacent a respective check box 50. Next to each check box 50 is a graphical component 52 that represents the magnitude of the Usefulness value. As can be seen from FIG. 3, the plurality of findings 51 are presented in ranked order, from the top of the screen to the bottom of the screen, wherein the relative magnitude of the Usefulness of each of the findings is presented by the graphical representation presented by the bars 52, each of which is associated with the respective one of the findings 51. Accordingly, a clinician by viewing the computer display can determine which of the findings is most likely to disambiguate between a plurality of candidate medical conditions. Lower ranked findings are accessible using the scroll bar.

As further depicted in FIG. 3, the clinician is provided with a set of graphical controls that allow the clinician to select constraints that can be employed when calculating the Usefulness of each of the findings. Specifically, FIG. 3 depicts that a plurality of check boxes 56, 58 and 60, as well as a choice box 54, can be provided as graphical controls through the display shown in FIG. 3. The choice box 54 allows the clinician to select the cost control that is applied to the Usefulness determination. In the depicted choice box 54, the clinician has selected the LOW-COST option, wherein, as described above, the Usefulness determination is constrained by the economic cost that is associated with collecting information about the finding. In a depicted display, the clinician has the opportunity to select the choice box 54 to present a series of alternative options for the cost constraint. As will be understood by one of ordinary skill, the choice box 54 can provide a number of selections including LOW COST, MID COST, and IGNORE COST. This, therefore, allows the clinician to select the cost constraint that is to be applied to the Usefulness determination, and is understood to follow from the above-described determinations of Usefulness in which cost can be a full consideration, partial consideration or not a consideration at all.

As further shown by FIG. 3, the clinician is also provided with graphical controls to select whether or not the Usefulness determination is to consider the curability, or availability of effective treatments, for the plural medical conditions under consideration. In this way, the clinician can select the curability box to constrain the Usefulness determination to rate most highly findings that are significant for selecting candidate diseases that have known effective treatments.

Figure 6:
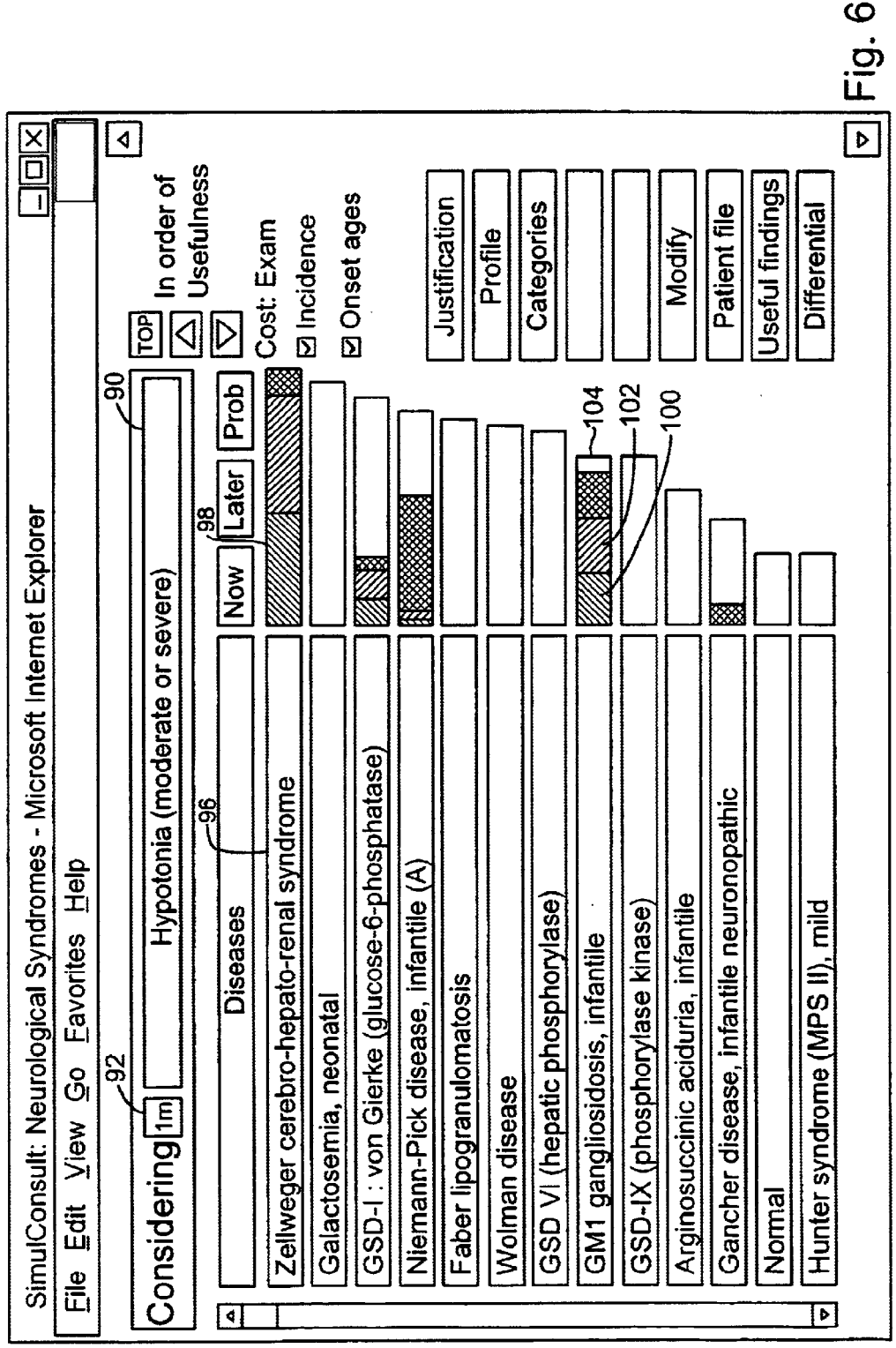
FIG. 6 depicts a screen shot illustrating a display that shows the effect of a finding being considered on the existing disease probability.

Other controls are provided to the clinician including controls for directing the Usefulness determination to allow input of the onset ages of the different findings in the patient. The onset information is displayed as abbreviations in check boxes eg. FIG. 3 and 6. Onset age information for findings affects disease probabilities and therefore also affects the Usefulness of findings. Similarly an incidence control is provided that allows the clinician to specify whether the program uses or ignores the different incidences of the diseases within the general patient population.

It can be seen, therefore, that the screen display depicted in FIG. 3 provides the clinician with a ranked list of findings, presented in order, and with a graphical depiction of the Usefulness measure of each respective finding. The screen also provides a set of controls that the user can employ to change the constraints applied to the Usefulness determination. Accordingly, the clinician can test the different constraints, to see which Findings are most useful in light of cost concerns, availability of effective treatment, or any other selectable constraint.

In another aspect, it will be understood that because the invention provides a system that can rank findings by Usefulness, it also provides a means for clinicians to enter fully coded information into an Electronic Medical Record. The Usefulness display gives the clinician an interface that is displaying in real-time the findings that are relevant for the clinician to check. This display can be updated at any point to reflect all the findings entered so far, and the effect of the Usefulness determination is to enable the display to be free of unimportant findings that would be distracting to a clinician with a patient in the room. Thus, the Usefulness determination enables the clinician to use this software as a method of note-taking during a clinical session.

This ability to use the software as a note-taking tool also adds another use of the software. One practiced in the art can ensure that the internal codes for both diseases and findings used in the database are tagged with standardized codes such as ICD-9 codes, UMLS codes or "Read" codes. The use of standard medical codes ensures that the information entered by the clinician is in a coded form that can be transferred as such to an Electronic Medical Record. This coding function occurs without any focusing by the clinician on the task of coding of information, thereby achieving results produced by software devoted exclusively to coding of medical information. Thus, the Usefulness determination allows the software to function both as a note-taking tool and an electronic coding tool for medical information.

Once the clinician has entered findings into the system, the program can provide a Justification screen that lists the findings deemed by the clinician to be present and findings deemed to be absent in the patient. One embodiment of such a screen is depicted FIG. 4. As shown in FIG. 4, the Justification screen provides a list of findings 62 along with a graphical component 64 that depicts the frequency of each finding in the particular disease being displayed. In the screen depicted by FIG. 4, the graphical component 64 is a colored bar that employs length to display the probability that eventually the finding will appear in a patient having the condition. This display allows for comparing the case for choosing the diagnosis of the highly-ranked diseases and the case against the lower ranked diseases.

In the Justification screen the frequency of each finding that is specified by the clinician as being present or absent can be represented using the colored bars 64. The colored bars 64 can be compound graphical elements that comprise two or more sub-elements, each of which convey information to the clinician. For example, the depicted colored bars 64 can include one component, such as the solid black component 66 that can represent the probability that the finding has an onset time during the period specified by the clinician, a period that is displayed in a box 72 adjacent to the name of the finding. This display of a black bar component 66 representing probabilities allows the clinician to search rapidly for diseases that have prominent black bars adjacent to findings that are present, and negligible black bars adjacent to findings that are absent.

Additionally, the black bar components 66 can appear to be an overlay on the composite element 64, which can be shown in another color, such as the component 70 which can be a green bar, representing the eventual probability that each finding will be found in the particular disease. When onset information is provided by the clinician indicating at what age a finding developed, the Justification screen can restrict the black bar components to represent this onset period and optionally can indicate other onset periods prior to that time with another sub-element, such as a bar of another color, such the component 68 which can be a gray bar, to indicate that they are not used as relevant probabilities in computing the probabilities of disease for this patient.

The Justification screen provides a justification to the clinician of why a particular disease is ranked high or low in probability. The clinician does not need to have concentrated on a particular diagnosis during the data-entry process to obtain a justification for its importance in the patient. A clinician can compare the justification for different diseases ranked in the order of the "differential diagnosis" ranking of disease probabilities, by pressing arrow button located on the screen that change the disease being considered.

Figure 5:
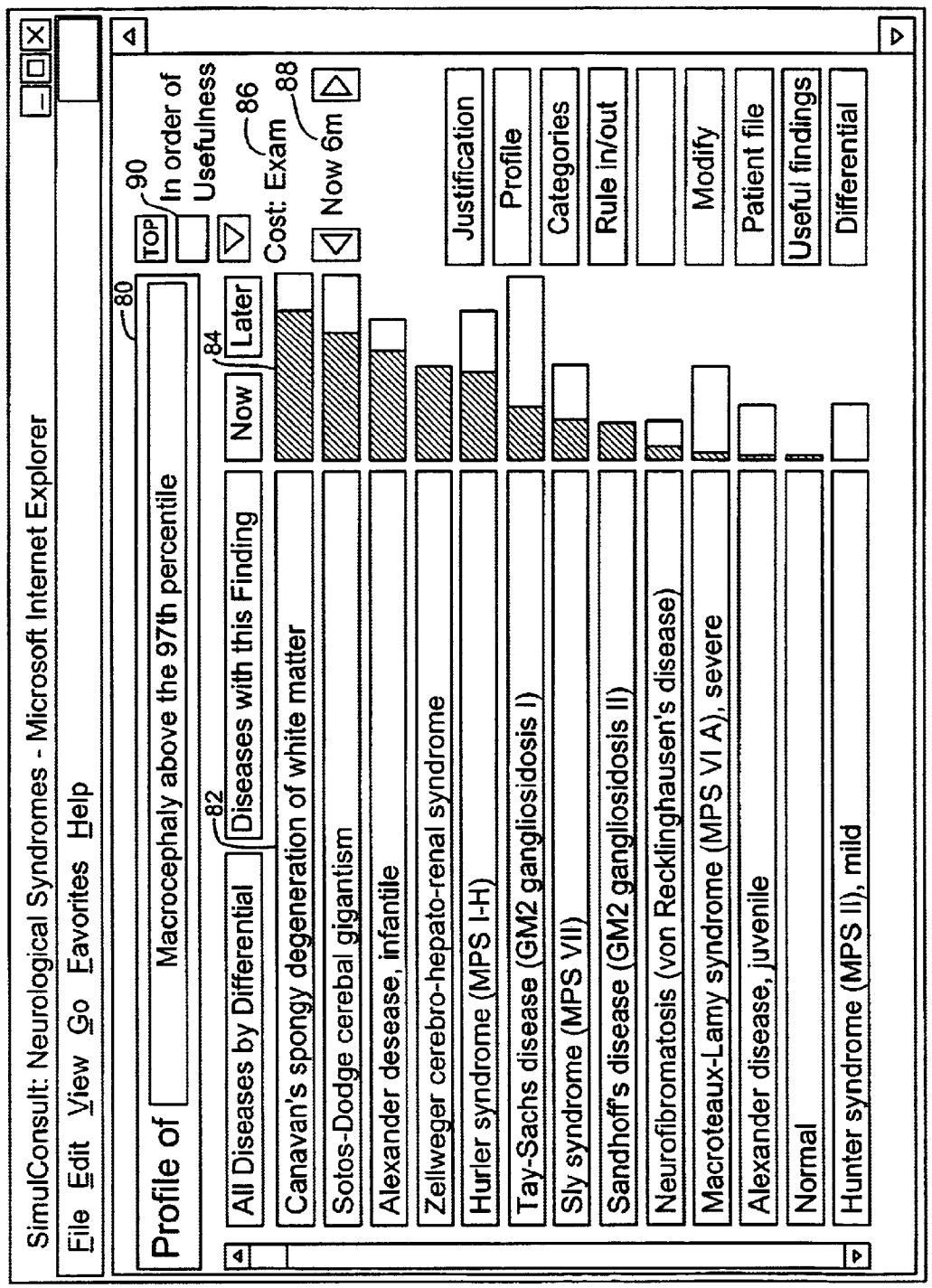
FIG. 5 depicts a screen shot illustrating a display that shows a profile of a particular finding or disease.

The program can also provide a profile screen that employs the information determined by the above described analysis to display an analysis of the determined facts in a manner that aids the clinician in answering questions ancillary to the diagnostic process, such as "what would a finding tell us about the disease being considered?" and "will an expensive test being ordered for a patient yield information that will be significant is disambiguating between candidate medical conditions?" One example of a profile screen is set forth in FIG. 5. The profile screen can present analytical information in a number of ways, including providing lists of findings in a particular disease and lists of diseases with a particular finding. In addition, these screens can also display for the disease being described, information about all findings, ranked by Usefulness, or for the finding being described, information about all diseases, ranked by probability. The profile screens also provide information about the evolution of a disease or finding over time, access using the sideways pointing arrow buttons, the screens also allow flipping between screens for different disease (ranked by probability) or flipping between screens for various findings (ranked by usefulness).

Turning to FIG. 5 one profile screen is depicted. The depicted screen includes a title box 80 that displays the finding being profiled, a list of diseases 82, a set of graphical elements 84 that display probability information for a respective one of the findings in the list 82, a cost factor display 86, a control 88 for selecting an onset time, and a rank control 90 for moving through different findings according to the relative Usefulness measure of those findings. As depicted, the clinician can employ the control 90 to move through the ranking of findings to select a particular finding, or to select findings that have been identified as particularly useful. In response to a selected finding, the screen can display the list of candidate diseases 82, ranked according to the probability that the selected finding would be present in the candidate disease. The screen further includes the cost factor display 86 that displays to the clinician the cost factor taken into consideration when the usefulness analysis was performed which provided the data now being organized and displayed by the profile screen. The screen also includes an onset age control 88 that allows the clinician to consider the probability that a particular finding would occur at a particular age. These probabilities, as well as the probabilities that the finding will eventually occur within a patient, can be displayed by the compound graphical elements 84. The depicted graphical elements 84 can operate similar to the elements 64 depicted in FIG. 4, where different coloring, or hatching can be employed to achieve and overlay effect that allows the graphical component to present a set of information to the clinician.

As can be seen from the Figure, these profile/description screens answer questions in clinical medicine. For example, a clinician is asked frequently by patients and insurers: "what would this finding (viz. diagnostic test) tell us about diseases being considered". The ability of this system to generate this information to describe the evidence-based-medicine rationale for doing a particular medical test allows a rapid and standardized exchange of information between the clinician and the insurer, which also demonstrates to the insurer that the clinician has gone through a process in which cost is considered during the Usefulness determination discussed above. The patient description can be sent electronically from the system to an insurer that could review the Usefulness, Differential, Consider and Description screens to evaluate whether the clinician is using cost-effective methods to diagnose the patient. This standardized display of the relevant information will speed, standardize and simplify the communication of patient information between the clinician and the insurer, as well as provide a guarantee that a cost-saving tool has been used to evaluate the patient's condition.

In a further embodiment of the invention, the system can include a "Consider" screen that can consist of a display of the probability of the diseases in the differential diagnosis with the probability bars filled in with the onset information of the considered finding in each disease. FIG. 6 depicts one example of such a computer screen. The screen includes a text box 90 that displays the finding being considered, a text box 92 that displays the age of interest for the analysis of usefulness, a list of candidate diseases 96, a set of graphical elements 98 that display probability information, and other user interface elements that display information about the diagnostic analysis to the clinician. The graphical element 98 depicted in FIG. 6 is a compound graphical element that provides information about the onset of the finding as well as information about the likelihood that the associated candidate medical condition is the correct diagnosis. The depicted onset information can be the same set of onset information displayed in the Justification screen of FIG. 4—with onset during the specified time period, before or after that period indicated using three distinct colors. The likelihood of onset for a finding occurring for the onset time presented in component 92 is indicated by the length of the component 100, the likelihood of onset during a previous time period is presented by the length of component 102 and, the likelihood of onset in a subsequent time period is presented by the component 104, with the total length of the components 100, 102 and 104 as a fraction of the length of the bar 98 indicating the likelihood of the finding occurring at all in the respective disease. The total length of bar 98 indicates the likelihood of the associated candidate disease being the correct diagnosis. This screen serves to indicate to clinicians the reasoning process used by the software, since the next probability screen after incorporating the new information can be deduced by observing the length of the bars denoting the probability of the finding being considered being present in the various diseases. The Consider screen also serves the purpose of displaying to insurers the importance of a particular finding in making a diagnosis, as discussed above. This can be employed for justifying the need or burden of a clinical procedure. The need or burden can be defined in terms of cost, risk, time or any other criteria or combination of criteria that can be employed for establishing limits on the availability of clinical procedures or other diagnostic aids.

The above described systems and methods, including the depicted screen shots, are only provided for illustrative purposes and it is to be understood that the invention can be realized in other embodiments. For example, the systems and methods described herein can be embodied in handheld systems, with hardware designed for carrying out the processes described herein. Moreover, the systems and methods described herein can include systems for allowing a non-medical professional to secure a computer generated second opinion, such as by allowing a patient, parent or guardian, to diagnose a medical condition, such as the patient's own medical condition. Those skilled in the art will know or be able to ascertain using no more than routine experimentation, many equivalents to the embodiments and practices described herein. Moreover, the development of programs for implementing the information displays described herein follows from principles of software engineering well known to those of ordinary skill in the art and it will be apparent that many modifications and additions can be made without departing from the scope of the invention. Accordingly, it will be understood that the invention is not to be limited to the embodiments disclosed herein, but is to be understood from the following claims, which are to be interpreted as broadly as allowed under the law.

I claim:

1. A process for diagnosing a medical condition of a patient, comprising the acts of
   identifying a plurality of candidate medical conditions,
   identifying a plurality of findings to provide a list of findings, each of which is representative of clinical information that can be gathered about the patient's condition,
   determining for each finding, a likelihood that a particular finding can disambiguate between said candidate medical conditions, and
   ranking said findings as a function of the likelihood that a finding can disambiguate between said plurality of medical conditions, whereby a clinician can employ said ranked findings to identify a finding that is likely to lead to a correct diagnosis of the patient's medical condition.

2. A process according to claim 1, further comprising the act of
   weighting the likelihood that a finding can disambiguate between a plurality of medical conditions by a factor representative of an economic cost of obtaining the clinical information representative of the finding.

3. A process according to claim 1, further comprising the act of
   weighting the likelihood that a finding can disambiguate between a plurality of medical conditions by a factor representative of a possibility that a disease can be treated effectively.

4. A process according to claim 1, further comprising the act of
   identifying a plurality of findings that can be determined from a single clinical procedure, and
   determining a composite score representative of the likelihood that said plurality of findings can disambiguate between said plural medical conditions.

5. A process according to claim 1, comprising the further act of
   selecting a plurality of findings that can be identified from a known battery of laboratory tests, and
   determining a composite score representative of the likelihood that said plurality of findings can disambiguate between said plural medical conditions.

6. A process according to claim 1, comprising the further act of
   allowing a clinician to enter finding data representative of the presence or absence of a finding presented in said list of findings, including the onset age of a finding in a patient, and
   reordering remaining findings from said list of findings, as a function of the presence or absence of finding data, according to the likelihood that a finding can disambiguate between said plurality of medical conditions.

7. A process according to claim 1, comprising the further acts of
   determining, as a function of the presence or absence of a finding, the onset age of a finding, and the probability of diseases, a usefulness signal representative of the change in likelihood that a patient has a particular disease.

8. A process according to claim 1, wherein determining for each finding a likelihood that a particular finding can disambiguate between said candidate medical conditions, comprises the act of
   determining for each finding a usefulness signal representative of a summation of the changes in probability estimates for said candidate medical conditions occurring in response to an indication of the presence or absence of the respective finding in the patient.

9. A process according to claim 1, comprising the further acts of
   allowing a clinician to select one of said plural medical conditions, and
   determining for the selected medical condition the likelihood that a finding can identify the selected medical condition as the condition afflicting the patient, whereby the clinician can rule in or rule out the selected medical condition.

10. A process according to claim 1, comprising the further act of
    displaying for a patient a listing of findings determined to be present for a patient and a list of findings determined to be absent for a patient, and
    displaying, for a selected medical condition, a set of probabilities each associated with a respective one of findings and each being representative of the likelihood that the respective finding is present in a patient having the selected medical condition, whereby the clinician is provided information for justifying a diagnosis.

11. A process according to claim 1, comprising the further act of
    displaying for a patient a listing of candidate medical conditions, and
    displaying for each candidate medical condition a likelihood that the respective medical condition is the correct diagnosis, whereby a clinician can monitor the change in likelihood of candidate medical conditions in response to the entry of finding data.

12. A process according to claim 11, comprising the further act of
 displaying for each candidate medical condition a likelihood that the respective medical condition is the correct diagnosis as a function of onset age of findings.

13. A process according to claim 1, comprising the further act of
 generating a data record representative of the likelihood a particular finding will disambiguate between plural medical conditions, and
 transmitting said data record to an authorization center for requesting authorization for performing a clinical procedure capable of determining the presence or absence of the particular finding in the patient.

14. A process according to claim 1, comprising the further act of
 determining the likelihood of a finding being capable of disambiguating between a plurality of medical diseases as a function of the age of the patient and the age of onset of the finding.

15. A process for displaying clinical diagnostic information, comprising the acts of
 employing a list of candidate medical conditions, each of which being associated with a ranking representative of the likelihood that the candidate medical disease is a correct diagnosis for a patient, and
 providing a graphical control element for allowing a clinician to flip between displays associated with said candidate medical conditions and presenting screens of finding information.

16. A process according to claim 15, wherein the graphical control element allows flipping between adjacent candidate medical diseases in the list.

17. A process according to claim 15, wherein the graphical control element allows flipping to the first candidate medical disease in the list.

18. A process for displaying clinical diagnostic information, comprising the acts of
 employing a list of findings, each being associated with a ranking representative of the likelihood that the finding can disambiguate between a plurality of candidate medical diseases, and
 providing a graphical control element for allowing a clinician to flip between displays associated with said findings and presenting screens of disease information.

19. A process according to claim 18, wherein the graphical control element allows flipping between displays associated with adjacent findings in the list.

20. A process according to claim 18, wherein the graphical control element allows flipping to a display associated with the first finding in the list.

21. A method of displaying clinical diagnostic information, comprising the acts of
 providing a plurality of findings and a set of probability values, each associated with a respective one of said plurality of findings and each being representative of the likelihood that the presence or absence of the finding can disambiguate between a plurality of medical conditions, and
 displaying on a computer display said plurality of findings, wherein said plurality of findings are arranged on the computer display to indicate the likelihood that one of the findings can disambiguate between a plurality of candidate medical conditions.

22. A computer readable medium having stored thereon instructions for directing a computer to
 provide a plurality of candidate medical conditions,
 provide a plurality of findings, each of which is representative of clinical information that can be gathered about the patient's condition,
 determine for each finding, a likelihood that a particular finding can disambiguate between said candidate medical conditions, and
 rank said findings as a function of the likelihood that a finding can disambiguate between said plurality of medical conditions, whereby a treating clinician can be provided with useful information regarding the likelihood that a finding can lead to the identification of the target medical condition.

23. A system for providing a clinician with a database of ranked findings for diagnosing a disease, comprising:
 a computer network having a server that will receive information on findings and store for each finding a record having information representative of the likelihood that the finding with an onset age is present in a patient having a particular disease,
 a computer program operating on said server to generate a data file representative of a plurality of such records, and
 a transfer program capable of transferring said data file to a client station, whereby a clinician at the client station is provided with a database of information ranked in an order representative of the likelihood that a finding is useful in diagnosing the disease.

24. A method for selecting a clinical procedure for diagnosing a disease, comprising the acts of
 identifying a plurality of candidate diseases, each having an associated likelihood that the candidate disease is a correct diagnosis for a patient's medical condition,
 identifying a plurality of candidate findings, each being representative of information that can be gathered about a patient's medical condition,
 selecting one of said candidate findings, and
 determining for each of said candidate diseases a change in likelihood that the candidate disease is the correct diagnosis as a function of whether the selected candidate finding is present or absent.

25. A method according to claim 24, comprising the further acts of
 selecting each of said candidate findings and determining for each of said candidate diseases the change in likelihood that the candidate disease is the correct diagnosis as a function of whether the selected candidate finding is present or absent, and
 generating for each finding a value representative of a summation over all said candidate diseases of the changes in likelihood of the candidate disease being the correct diagnosis.

26. A method according to claim 24, comprising the further act of
 determining the change in likelihood that a candidate disease is a correct diagnosis as a function of the age of the patient or the age of onset of the finding.

27. A method according to claim 24, comprising the further act of
 determining the change in likelihood that a candidate disease is a correct diagnosis as a function of a cost of performing a clinical procedure for determining the presence or absence of the finding.

28. A method according to claim 24, comprising the further act of determining the change in likelihood that a candidate disease is a correct diagnosis as a function of a probability representative of the likelihood that the candidate disease can be treated effectively.

29. A process for diagnosing a medical condition of a patient, comprising the acts of providing a list of candidate medical conditions each being associated with a probability estimate representative of the likelihood that the candidate medical condition is a correct diagnosis, providing finding information for the patient, including information representative of findings identified in the patient and including onset information representative of a time of onset associated with the finding, and generating as a function of the onset information and the probability estimates, a compound graphical component for each of the candidate medical conditions capable of displaying probability data representative of a selected finding being present in the candidate disease during a specified onset period, whereby finding information can be entered to generate a set of graphical components that include a component that predicts new probability estimates that can result in response to specifying a selected finding.

30. A system for creating medical records for a patient, comprising means for identifying a set of findings for diagnosing a medical condition and for displaying the set findings in an order representative of the likelihood that a finding can disambiguate between a plurality of medical conditions, means for allowing a clinician to enter information representative of those findings identified in the patient, and means for generating a data record representative of information gathered during a diagnostic process, said information including standard code signals for diseases and findings.

31. A method for justifying a clinical procedure, comprising (a) providing a list of candidate findings, each being representative of information that can be gathered about a patient's medical condition during a clinical procedure, (b) providing a list of candidate diseases, each having an associated likelihood that the candidate disease is a correct diagnosis for a patient's medical condition, (c) selecting one of said candidate findings, (d) determining for each of said candidate diseases a change in likelihood that the candidate disease is the correct diagnosis as a function of whether the selected candidate finding is present or absent, and summing the determined changes in likelihood to generate a measure of the usefulness of the selected candidate finding, (e) repeating steps (c) and (d) to determine a measure of usefulness for at least a portion of the candidate findings in the list of candidate findings, and (f) for at least a portion of the candidate findings, comparing the measure of usefulness for a candidate finding to a measure of burden, to determine if a clinical procedure for collecting information regarding the candidate medical condition is justified.

* * * * *